US009764342B2

(12) United States Patent
Vellutato, Jr. et al.

(10) Patent No.: US 9,764,342 B2
(45) Date of Patent: *Sep. 19, 2017

(54) MIXING AND DISPENSING APPARATUS

(71) Applicant: Veltek Associates, Inc., Malvern, PA (US)

(72) Inventors: Arthur L. Vellutato, Jr., Malvern, PA (US); Walter A. Baker, Chalfont, PA (US)

(73) Assignee: VELTEK ASSOCIATES, INC, Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/643,496

(22) Filed: Mar. 10, 2015

(65) Prior Publication Data
US 2015/0209809 A1  Jul. 30, 2015

Related U.S. Application Data

(63) Continuation of application No. 13/974,746, filed on Aug. 23, 2013, now Pat. No. 9,108,208, which is a (Continued)

(51) Int. Cl.
*B67D 7/74* (2010.01)
*B05B 7/26* (2006.01)
(Continued)

(52) U.S. Cl.
CPC ........ *B05B 7/26* (2013.01); *A61L 2/22* (2013.01); *A61L 9/14* (2013.01); *B05B 11/0081* (2013.01);
(Continued)

(58) Field of Classification Search
CPC ............ B05B 11/0081; B05B 11/0083; B05B 11/0078; B05B 11/0048; B05B 7/26;
(Continued)

(56) References Cited

U.S. PATENT DOCUMENTS 2,631,521 A * 3/1953 Atkins, Jr. ............ B65D 51/224
206/222
2,753,990 A  7/1956 Chalfin et al.
(Continued)

FOREIGN PATENT DOCUMENTS

DE   460 043 C    5/1928
DE   20022904 U1  8/2002
(Continued)

OTHER PUBLICATIONS

USP 26, General Information (1211) Sterilization and Sterility Assurance of Compendial, pp. 2433-2438, 2003.
(Continued)

*Primary Examiner* — Patrick M Buechner
(74) *Attorney, Agent, or Firm* — Blank Rome LLP

(57) ABSTRACT

A mixing and dispensing apparatus having first and second containers. The first container has a main body portion which retains a first substance. A separate compartment is located in the first container and an internal passageway is formed between the main body portion and the compartment. The second container is configured to retain a second substance, and is compressible. The second container has a top end and a closed spout, wherein the closed spout is located in the compartment with the spout extending through the internal passageway into the main body portion of said first container. A release mechanism is formed by a plunger extending within the second container. The plunger has a first end in communication with the top end of the second container, and a second end aligned with the closed spout. The second end opens the closed spout when the second container is compressed to release the second substance into the main body portion of the first container.

21 Claims, 5 Drawing Sheets

Related U.S. Application Data continuation of application No. 13/239,611, filed on Sep. 22, 2011, now Pat. No. 8,523,017.

(51) Int. Cl.
*B05B 11/00* (2006.01)
*A61L 2/22* (2006.01)
*A61L 9/14* (2006.01)
*B05B 11/04* (2006.01)

(52) U.S. Cl.
CPC ........ *B05B 11/0089* (2013.01); *B05B 11/048* (2013.01); *B05B 11/30* (2013.01); *A61L 2202/25* (2013.01); *A61L 2209/14* (2013.01); *A61L 2209/211* (2013.01)

(58) Field of Classification Search
CPC ... B01F 13/027; B65D 25/08; B65D 51/2857; B65D 51/2814; B65D 51/2835; A61L 2/16; A61L 2/18; A61L 2202/18; A61L 2202/10; A61L 2202/181; A61L 2202/182; A61L 2/22; A61L 2202/25; A61L 9/14; A61L 2209/14; A61L 2209/211
USPC ............. 222/80, 81, 82, 83, 83.5, 88, 541.2, 222/145.5, 206, 207, 129, 130, 131, 325, 222/145.6, 145.1, 321.8, 383.1; 433/90; 366/602, 130; 206/538, 219, 222; 215/DIG. 8; 604/82, 87, 89, 191, 416
See application file for complete search history.

(56) References Cited

U.S. PATENT DOCUMENTS

| | | |
|---|---|---|
| 2,781,141 A | 2/1957 | Lucien |
| 3,156,369 A | 11/1964 | Bowes et al. |
| 3,236,697 A | 2/1966 | Amiet et al. |
| 3,326,400 A | 6/1967 | Hamelin et al. |
| 3,347,410 A * | 10/1967 | Schwartzman ........ A45D 19/02 206/222 |
| 3,458,076 A | 7/1969 | Babcock |
| 3,856,138 A | 12/1974 | Maekawa et al. |
| 3,952,341 A | 4/1976 | Cain |
| 3,966,089 A | 6/1976 | Klingaman |
| 3,968,872 A | 7/1976 | Cavazza |
| 4,177,938 A | 12/1979 | Brina |
| 4,193,698 A | 3/1980 | Gartner |
| 4,195,730 A | 4/1980 | Hunt |
| 4,195,731 A | 4/1980 | Cavazza |
| 4,221,291 A | 9/1980 | Hunt |
| 4,264,007 A | 4/1981 | Hunt |
| 4,529,511 A | 7/1985 | Breeden et al. |
| 4,591,050 A | 5/1986 | Finke et al. |
| 4,606,734 A | 8/1986 | Larkin et al. |
| 4,615,437 A | 10/1986 | Finke et al. |
| 4,705,191 A * | 11/1987 | Itzel .................... B05B 11/0037 141/326 |
| 4,750,634 A | 6/1988 | Herman |
| 4,757,916 A | 7/1988 | Goncalves |
| 4,763,460 A | 8/1988 | Higo et al. |
| 4,775,564 A | 10/1988 | Shriver et al. |
| 4,793,475 A | 12/1988 | Itzel |
| 4,832,230 A | 5/1989 | Janowitz |
| 4,903,865 A | 2/1990 | Janowitz |
| 4,950,237 A | 8/1990 | Henault et al. |
| 4,982,875 A | 1/1991 | Pozzi et al. |
| 5,029,718 A | 7/1991 | Rizzardi |
| 5,038,951 A | 8/1991 | Rizzardi |
| 5,071,034 A | 12/1991 | Corbiere |
| 5,114,011 A | 5/1992 | Robbins, III |
| 5,195,966 A | 3/1993 | Corby |
| 5,215,225 A | 6/1993 | Kopp |
| 5,310,085 A | 5/1994 | Lontrade et al. |
| 5,350,087 A | 9/1994 | Frazier et al. |
| 5,353,961 A | 10/1994 | Debush |
| 5,383,579 A | 1/1995 | Lanfranconi et al. |
| 5,421,483 A | 6/1995 | Parise et al. |
| 5,543,097 A | 8/1996 | Fang |
| 5,555,007 A | 9/1996 | Ceschin et al. |
| 5,613,623 A | 3/1997 | Hildebrandt |
| 5,766,149 A | 6/1998 | Kriesel et al. |
| 5,772,017 A | 6/1998 | Kang |
| 5,811,060 A | 9/1998 | Laguna Valderrama |
| 5,836,479 A * | 11/1998 | Klima ................ B05B 11/0056 222/130 |
| 5,860,569 A | 1/1999 | Gregoire |
| 5,875,889 A | 3/1999 | Albisetti |
| 5,890,624 A * | 4/1999 | Klima .................... B05B 11/00 222/129 |
| 5,941,380 A | 8/1999 | Rothman |
| 5,947,332 A * | 9/1999 | Klima, Jr. ........... B05B 11/0056 222/130 |
| 5,950,819 A | 9/1999 | Sellars |
| 6,022,134 A * | 2/2000 | Andrews ............... B01F 13/002 206/221 |
| 6,041,969 A | 3/2000 | Parise |
| 6,073,803 A | 6/2000 | Sturm et al. |
| 6,123,900 A | 9/2000 | Vellutato |
| 6,150,423 A | 11/2000 | Carpenter |
| 6,152,296 A | 11/2000 | Shih |
| 6,165,523 A | 12/2000 | Story |
| 6,305,576 B1 * | 10/2001 | Leoncavallo ....... B65D 51/2814 206/222 |
| 6,319,453 B1 * | 11/2001 | Klima, Jr. ........... B05B 11/0056 264/504 |
| 6,568,562 B1 | 5/2003 | Klima, Jr. et al. |
| 6,688,146 B2 | 2/2004 | Michels et al. |
| 6,719,130 B1 | 4/2004 | Wagner |
| 6,736,169 B2 | 5/2004 | De Laforcade |
| 6,851,580 B2 | 2/2005 | Stank et al. |
| 6,928,674 B2 | 8/2005 | Blackburn |
| 7,066,354 B2 | 6/2006 | Stank et al. |
| 7,147,880 B2 | 12/2006 | Lenahan |
| 7,789,854 B2 | 9/2010 | Talamonti |
| 8,523,017 B2 | 9/2013 | Vellutato, Jr. et al. |
| 9,108,208 B2 * | 8/2015 | Vellutato, Jr. ....... B05B 11/0081 |
| 2001/0011661 A1 | 8/2001 | Klima et al. |
| 2004/0140321 A1 | 7/2004 | Stank et al. |
| 2004/0238566 A1 | 12/2004 | Stank et al. |
| 2005/0163651 A1 | 7/2005 | Vellutato |
| 2006/0226171 A1 | 10/2006 | Sternberg |
| 2007/0246380 A1 | 10/2007 | Esteban Villalobos |
| 2008/0035668 A1 | 2/2008 | Foster |
| 2008/0073375 A1 | 3/2008 | Nelson et al. |
| 2008/0135424 A1 | 6/2008 | Ostrowski |
| 2008/0202950 A1 | 8/2008 | Anderson |
| 2009/0260999 A1 * | 10/2009 | Yang .................... B65D 47/141 206/219 |
| 2009/0289025 A1 | 11/2009 | Mueller et al. |
| 2009/0308889 A1 | 12/2009 | Lindsay et al. |
| 2010/0084430 A1 | 4/2010 | Sim |
| 2010/0089947 A1 | 4/2010 | Sim |
| 2010/0147887 A1 | 6/2010 | Sim |
| 2013/0075495 A1 | 3/2013 | Vellutato et al. |
| 2013/0341349 A1 | 12/2013 | Vellutato et al. |
| 2014/0078857 A1 | 3/2014 | Nelson et al. |
| 2014/0202895 A1 | 7/2014 | Larson |
| 2015/0102061 A1 * | 4/2015 | Larson ................ B05B 11/0081 222/129 |

FOREIGN PATENT DOCUMENTS

| EP | 0300886 A1 | 1/1989 |
|---|---|---|
| FR | 2707601 A3 | 1/1995 |
| FR | 2708913 A1 | 2/1995 |
| FR | 2814156 A1 | 3/2002 |
| KR | 10-2010-0122825 | 6/2012 |
| WO | WO-02085 775 A1 | 10/2002 |
| WO | WO-2006/048866 A1 | 5/2006 |

(56) References Cited

FOREIGN PATENT DOCUMENTS

| WO | WO-2008153660 A1 | 12/2008 |
| WO | WO-2010025392 A2 | 3/2010 |
| WO | WO-2011027177 A1 | 3/2011 |

OTHER PUBLICATIONS

Clean Rooms, BBL Sterile Contact Plate, Becton Dickinson Microbiology Systems, vol. 5, No. 3, Cockeysville, MD, Mar. 1991.
Clean Rooms, Sterile Contact Plate, Becton Dickinson Microbiology Systems, Cockeysville, MD, Jun. 1991.
European Search Report dated May 6, 2004, cited in EP 04100136.3.
English-language translation of Chinese Office Action from a co-pending application, 6 pages.
English translation of Office Action dated Mar. 3, 2016 (9 pages).

\* cited by examiner

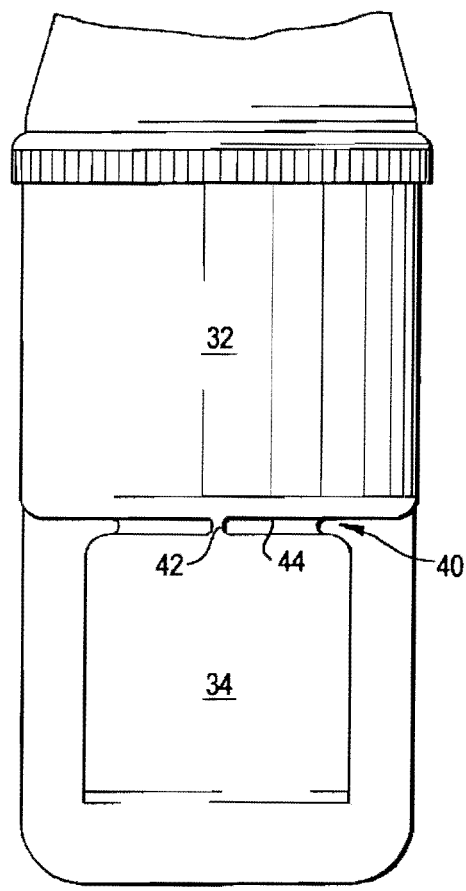
FIG. 2
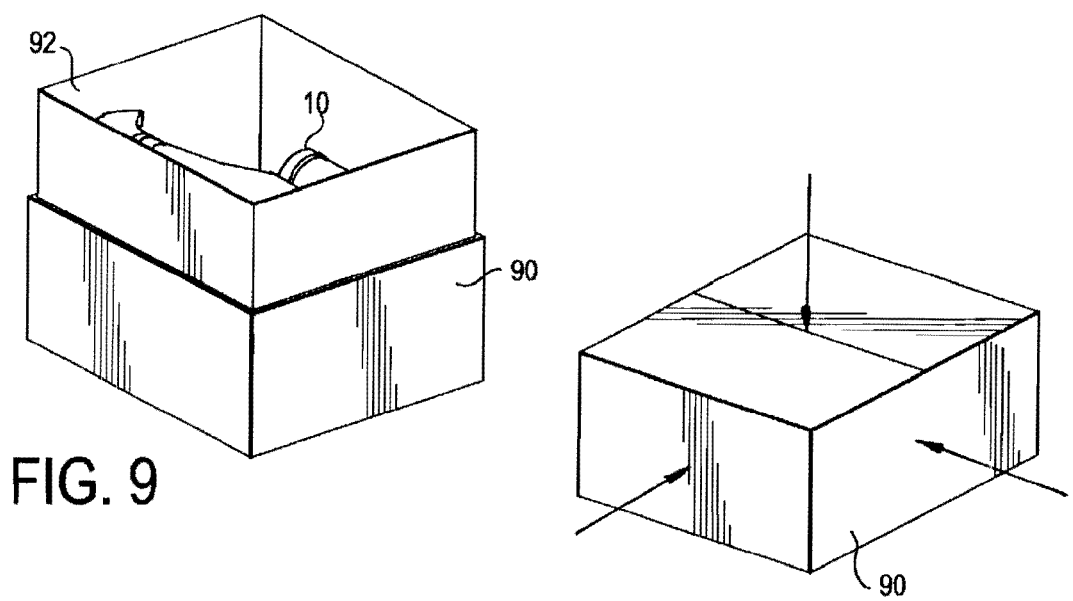
FIG. 9
FIG. 10

MIXING AND DISPENSING APPARATUS

RELATED APPLICATIONS

This application is a continuation of U.S. patent application Ser. No. 13/974,746 riled on Aug. 23, 2013, which is a continuation of U.S. Pat. No. 8,523,017, granted on Sep. 3, 2013, the contents of which is hereby incorporated by reference.

BACKGROUND OF THE INVENTION

Field of the Invention

The present invention relates to an apparatus for storing and shipping a composition to be used in a clean environment. More particularly, the present invention relates to an apparatus which separately stores two substances, mixes the two substances when ready to be used in the clean environment, and dispenses the mixed substances inside the clean environment.

Background of the Related Art

A clean room is a space designed, maintained, and controlled to prevent particle and microbiological contamination of products. Certain chemical compositions are used inside clean rooms including, for instance, germicidal disinfectants such as phenols, cleaners, quaternary ammonium, peracetic acid, as well as various sporicides, such as peracetic acid, bleach, and hydrogen peroxide. The disinfectants and sporicides are used in clean rooms to disinfect clean room surfaces. The compositions, which are not naturally sterile, can be sterilized by filtration inside of the clean room.

To sterilize the compositions outside the clean room, the concentrated composition is either terminally sterilized by irradiation or aseptically processed. To terminally irradiation sterilize the composition, the composition is placed in a container, double bagged, and placed in a lined carton. The entire carton is then terminally sterilized by irradiation. A procedure for terminally irradiation sterilizing a composition is described, for instance, in U.S. Pat. No. 6,123,900 to Vellutato, the disclosure of which is incorporated herein by reference.

To aseptically process the concentrated composition, the composition is sterilized through filtration and (inside a sterile environment) placed into a container that has been presterilized, such as by irradiation. The container can then be double bagged, also within the sterile environment. The double-bagged package is then removed from the sterile environment and placed into a carton having a liner. Aseptic processing is generally more labor intensive and expensive than terminal irradiation sterilization, and is typically only used for chemicals that cannot be irradiation sterilized, such as peracetic acid, bleach and hydrogen peroxide.

When concentrated compositions are used, they first must be diluted with sterile water to the proper concentration for use. However, the dilution breaks down the compositions, and consequently the diluted compositions have a relatively short shelf life of between about 17-30 days. Accordingly, clean room personnel typically dilute the concentrated composition just prior to actual use. To do so, once the sterile concentrated composition enters the clean room (either through on-site filter sterilization, or off-site irradiation sterilization or aseptic processing), it is typically manually mixed with a diluent (i.e., the sterile water) in a sterile container, such as a bucket, inside the clean room. The dilution and mixing has to be precise to ensure that the resulting concentration of disinfectant or sporicide will effectively kill the desired microorganisms. The mixing is difficult to perform manually since the person performing the mixing is outfitted in clean room apparel, such as sterile garments and gloves. Accordingly, the mixing is a time-consuming process that detracts from the time being spent on other work being performed in the clean room.

A number of containers have been developed which separately store two substances and allow the two substances to be mixed together prior to being dispensed as shown, for instance, in U.S. Pat. No. 6,305,576 to Leoncavallo, U.S. Pat. No. 6,152,296 to Shih, and U.S. Pat. No. 6,073,803 to Sturm. However, these patents are not well-suited for use to in a clean environment, including that they are not designed for shipment and sterilization, and can be difficult to use in a clean environment. In addition, the present invention improves upon the Assignees previous inventions, including U.S. Pub. No. 2005/0163651 to Vellutato, and U.S. Pat. No. 7,066,354 to Stank.

SUMMARY OF THE INVENTION

Accordingly, it is an object of the invention to provide a mixing and dispensing apparatus. It is another object of the invention to provide a mixing and dispensing apparatus which is easy to use in a clean room by a user that is fully gowned and gloved. It is a further object of the invention to provide a mixing and dispensing apparatus which is suitable for use in a clean room.

A mixing and dispensing apparatus having first and second containers. The first container has a main body portion which retains a first substance. A separate compartment is located in the first container and an internal passageway is formed between the main body portion and the compartment. The second container is configured to retain a second substance, and is compressible. The second container has a top end and a closed spout, wherein the closed spout is located in the compartment with the spout extending through the internal passageway into the main body portion of said first container. A release mechanism is formed by a plunger extending within the second container. The plunger has a first end in communication with the top end of the second container, and a second end aligned with the closed spout. The second end opens the closed spout when the second container is compressed to release the second substance into the main body portion of the first container.

These and other objects of the invention, as well as many of the intended advantages thereof, will become more readily apparent when reference is made to the following description, taken in conjunction with the accompanying drawings.

BRIEF DESCRIPTION OF THE FIGURES

FIG. 2 is a rear view of the large container showing the compartment and neck taken along line A-A of FIG. 1;

FIG. 9 is a perspective view showing the mixing and dispensing apparatus of FIG. 1 placed in a carton having a liner, in preparation for irradiation sterilization; and FIG. 10 is a perspective view showing the carton of FIG. 9 closed and being irradiated in a plurality of different directions.

DETAILED DESCRIPTION OF THE PREFERRED EMBODIMENTS

Figure 1:
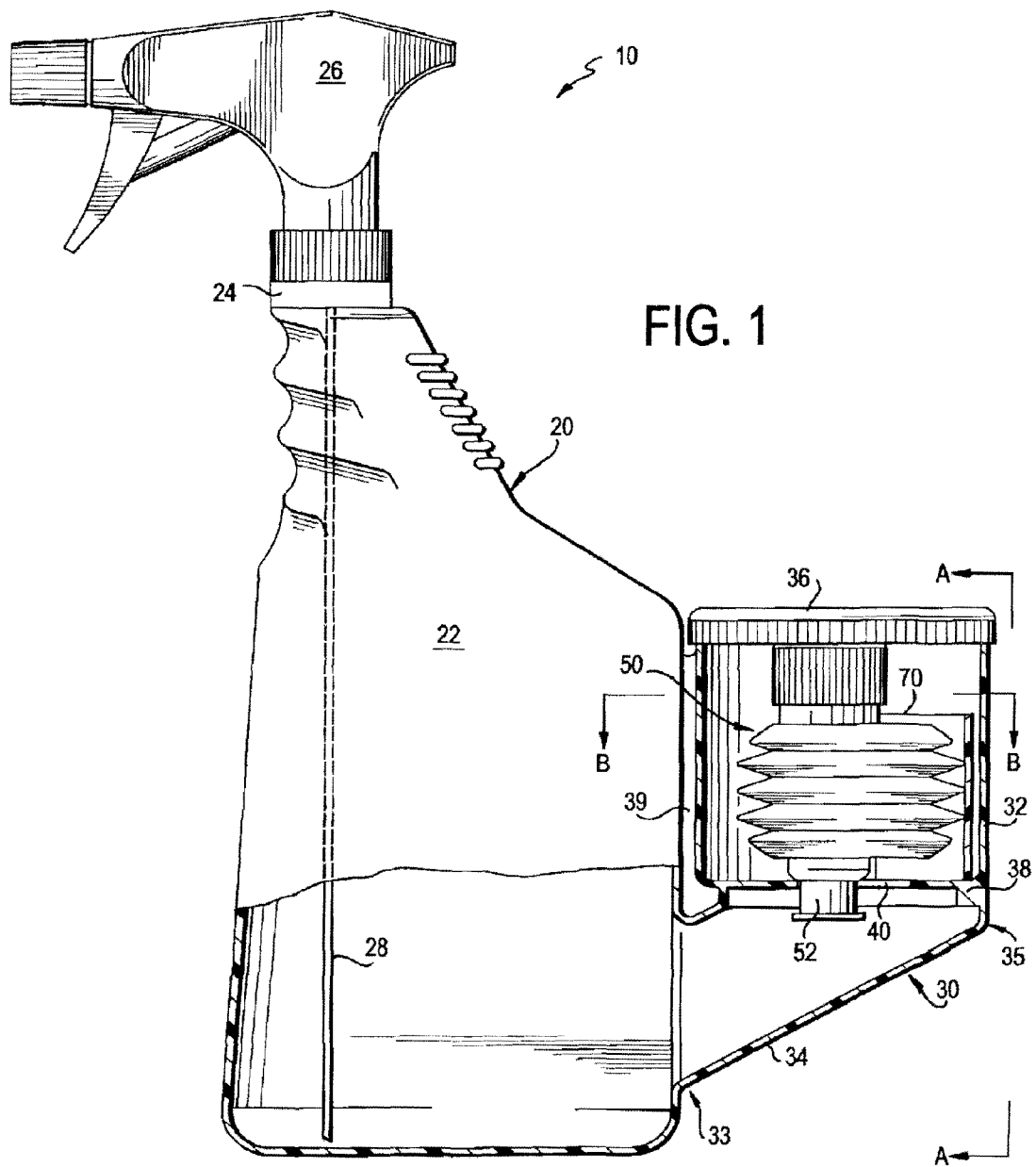
FIG. 1 is a side view of the mixing and dispensing apparatus in accordance with the preferred embodiment of the invention showing the large container with a cutaway view of the side compartment housing a second container.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose.

Turning to the drawings, FIG. 1 shows the mixing and dispensing apparatus 10 of the present invention. The apparatus includes a first large container 20 and a second small container 50. The large container 20 is preferably a spray bottle configured to receive the small container 50, and the small container 50 is preferably a round bellowed bottle. The containers 20, 50 are sized so that the small container 50 fits inside a compartment of the large container 20.

The large container 20 has a main body portion 22 which retains a first liquid, such as a diluent. An opening 24 is located at the top of the main body portion 22. The reservoir of the main body portion 22 of the large container 20 holds a predetermined amount of diluent, preferably about 8-32 ounces of sterile water, for use in the method of the invention. The small container 50 retains up to about 0.5-2 ounces of liquid.

The opening 24 is externally threaded to receive an optional dispensing mechanism 24. In the embodiment of FIG. 1, the dispensing mechanism 24 is a manually-actuated spray head having a trigger and an adjustable nozzle. The nozzle can emit a nebulized spray or a stream spray. It should be appreciated, however, that other suitable dispensing mechanisms 24 can be utilized within the spirit and scope of the invention, or that there need not be any dispensing mechanism 24 but rather that a cap is provided to close the opening 24. A dip tube 28 extends from the dispenser mechanism 26 into the main body portion 22 to retrieve liquid stored in the reservoir of the main body portion 22. Upon manual actuation of the trigger, the dispensing mechanism 26 retrieves the liquid from the main body portion 22 through the dip tube 28 and forces it out of the nozzle of the dispensing mechanism 26.

A receiving portion 30 is integrally molded with the main body portion 22. The receiving portion 30 includes a compartment 32 and a neck 34. The compartment 32 generally has a circular shape with a top 36 and a bottom portion 38.

An opening is located at the top 36 of the compartment 32 and is threaded to receive a cover. The compartment 32 is separate from the main body portion 22 and extends to one side of the main body portion 22. The compartment 32 has sides which are substantially parallel to the sides of the main body portion 22. The side of the compartment 32 closest to and facing the main body portion 22 is connected to the side of the main body portion 22 closest to the compartment 32, by a thin elongated web member 39. The web member 39 preferably extends a substantial amount of the height of the compartment 32 side. The web member 392 affixes the compartment 32 to the main body portion 2 and supports the compartment against side-to-side movement.

The compartment 32 forms a chamber that receives the second container 50. The top 36 opening permits the small container 50 to be introduced into and fully positioned inside the compartment 32 of the large container 20.

The neck has one end 33 in flow communication with the main body portion 22, an opposite end 35 in flow communication with the small container 50 in the compartment 32, and an intermediate portion between the two ends 33, 35. Thus, the neck 34 connects the compartment 32 to the main body portion 22 so that the small container 50 is in fluid communication with the main body portion 22. The neck extends from a side of the main body portion 22 toward the bottom of the main body portion 22, to the bottom portion 38 of the compartment 32. The compartment 32 and the main body portion 22 are substantially parallel to one another, with the compartment 32 extending immediately at one side of the main body 22. The neck 34 has a ramp at the bottom which is at an angle to the main body portion 22, preferably about 30-45 degrees. And, the ends 33, 35 are substantially perpendicular to each other; with the end 33 at the main body portion 22 being substantially vertical and the end 35 at the compartment 32 when the dispenser 10 is sitting on the bottom of the main body 22. As shown in FIG. 2, the neck 34 is fairly wide, though narrower than the main body portion 22 and the compartment 32, which are approximately the same width as each other.

As shown in FIGS. 1 and 2, a passageway 40 is located between the compartment 32 and the neck 34. The passageway 40 is formed by an annular depression 42 that creates a plate or platform 44, so that the passageway 40 is integrally molded as part of the large container 20, together with the compartment 32 and the neck 34. The internal side of the platform 44 forms the floor at the bottom portion 38 of the compartment 32. The passageway 40 is formed in the platform 44 so as to provide an opening into the neck 34 from the compartment 32. The small container 50 can be placed in the compartment 32 of the large container 20 through the top opening 36, and the spout 52 of the small container 50 positioned in the passageway 40. The spout 52 of the small container 50 can then be opened and the contents of the small container 50 emptied into the reservoir of the large container 20. The top surface of platform 38 supports the small container 40 in the chamber of neck 24.

Figure 3A:
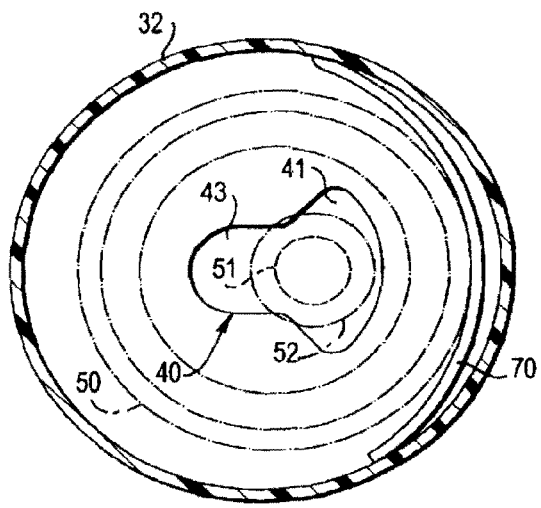
FIG. 3(a) is a top view of the compartment taken along line B-B of FIG. 1 showing the spout of the small container inserted in the wide portion of the passageway between the compartment and the large container.

The internal passageway 40 is further shown in FIGS. 3(a), (b) looking into the inside of the compartment 32. The passageway 40 is shown as an opening formed in the bottom of the compartment 32, where the bottom is formed by the inward depressions 42 formed in the container 20. The edges of the depression 42 form the passageway 40. As shown, the passageway 40 has a generally keyhole shape with a wide portion 41 and a narrow portion 43. The passageway 40 is symmetrical about its central longitudinal axis, with wide portion 41 formed as two opposing wings having tips. The passageway 40 narrows inward from the wing tips, then straightens at the narrow portion 41. The distal ends of the narrow portion 43 and the wide portion 41 are curved. The wide portion 41 is located off-center with respect to the center of the compartment 32.

Figure 3B:
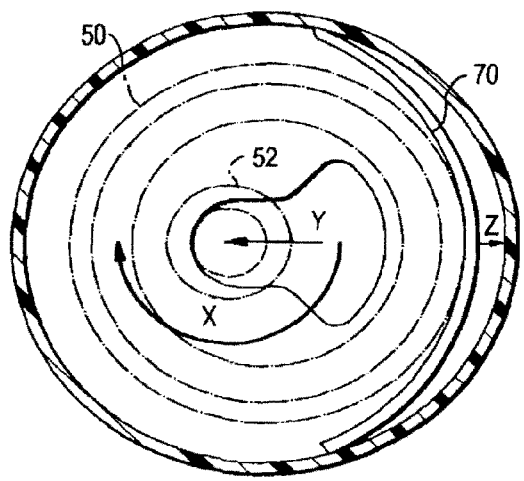
FIG. 3(b) is a top view of the compartment taken along line B-B of FIG. 1 with the small container rotated 180° so that the spout of the small container is in the locked position at the narrow portion of the passageway.

As best shown in FIGS. 1, 3(a), 3(b), a flexible plastic barrier 70 is preferably also positioned inside the compartment 42 about a portion of the small container 50. The barrier 70 stabilizes the small container 50 within the compartment 32 and keep it properly positioned in the passageway 40. The barrier 70 is generally formed as a rectangle with a length that is slightly smaller than the diameter of the compartment 32. Accordingly, the barrier 70 can bend within the compartment 32 and be supported by the inside of the walls of the compartment 32 at approximately a diameter of the compartment 32. The barrier 70 has a height about the same as the height of the bellows on the small container 50, so that the full height of the small container 50 is supported against the barrier 70.

Figure 4:
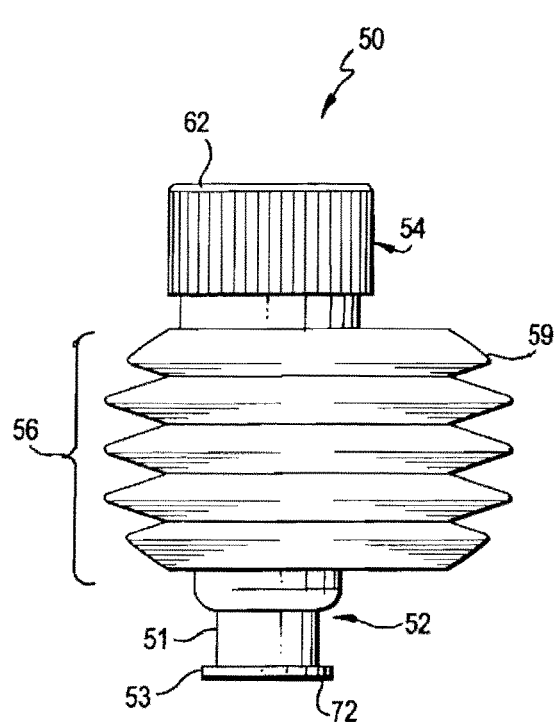
FIG. 4 is a side view of the small container.

The small container 50 is shown in FIG. 4 in greater detail. The small container 50 has a bottom cylindrical opening or spout 52, a top end 54 opposite the bottom end which is formed as a spout 52, and an intermediate portion 56 therebetween. The spout 52 extends outward from the intermediate portion 56 to form a cylindrical neck 51. A lip 53 is formed at the extreme distal end of the spout 52. The lip 53 is wider than the neck 51. The top end 54 also preferably projects outward from the intermediate portion 56 in a direction opposite to the bottom spout 52. The top opening is externally threaded to threadably engage an internally threaded cap.

In accordance with a preferred embodiment of the invention, the intermediate portion 56 of the small container 50 comprises a bellowed reservoir body which retains a liquid. Accordingly, the intermediate portion has a number of compressible bellows 59. Though the entire intermediate portion 56 is shown having bellows 59, it will be apparent that only a section of the intermediate portion 56 can have bellows 59. The intermediate portion 56 is wider than the spout 52. The intermediate portion 56 can have a smaller section which leads into the neck 51. The bellows 59 are arranged in an accordion-like style so that the top end 54 can be compressed toward the bottom end spout 52, and can also be extended so that the top end 54 can be moved apart from the bottom end spout 52.

Figure 5:
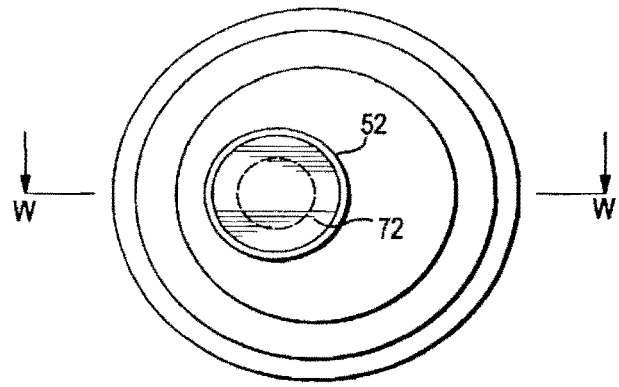
FIG. 5 is a bottom view of the small container showing the offset spout.

Turning to FIGS. 3(a), (b), the manner in which the small container 50 engages the internal passageway 40 of the large container 20 is shown. Referring momentarily to FIG. 5, the spout 52 is off-centered with respect to the intermediate body portion 56 of the small container 50. Accordingly, returning to FIG. 3(a), the small container 50 can be placed inside the compartment 32 of the large container 20 with the small container 50 oriented so that the spout 52 is aligned with the wide portion 41 of the passageway 40.

When inserted into the chamber of the compartment 32, the small container 50 is lowered so that the spout 52 is aligned with and received by the wide portion 41 of the passageway 40. As shown by the dashed lines, the small container 50 is offset within the compartment 32 for the alignment to be made. The lip 53 and neck 51 pass through the passageway 40, but the wider portion of the intermediate portion 56 is wider than the wide portion 41 of the passageway 40. Accordingly, the spout 52 comes to rest in the passageway 40 with the neck 51 positioned in the passageway 40 itself, the lip 53 positioned outside the passageway 40 in the neck 34 of the large container 20, and the intermediate portion 56 positioned in the compartment 32.

At that point, the small container 50 is positioned inside the compartment 32 and the spout is aligned in the wide portion 41 of the passageway 40; but the small container 50 is not yet fixed to the large container 20. The small container 50 is then given a half turn (180°), as represented by the arrow X in FIG. 3(b). As the small container 50 is rotated, the spout 52 of the small container 50 travels in the direction of arrow Y (to the left in the embodiment shown) by virtue of being offset on the small container 50, such that the spout 52 enters the narrow portion 42 of the passageway 40. In addition, the small container 50 is realigned within the compartment 32 in the direction of the arrow Z (to the right in the embodiment) since the spout 52 is offset. The spout 52 is able to enter the narrow portion 42 of the passageway 40 since the neck 51 of the spout 52 is smaller than the narrow portion 42. However, the lip 53 and widened intermediate portion 56 are wider than the narrow portion 42. The lip 53 prevents the spout 52 from being pulled upward out of the narrow portion 42 of the passageway 40. Accordingly, the small container 50 is in a fixed position within the passageway 40 so that the small container 50 is engaged with the large container 20. In the fixed position, the spout 52 is aligned through the passageway 40 with the neck 34 of the large container 20 so that any fluid released from the spout 52 will directly enter and mix with fluid in the large container 20 without any obstruction.

In FIG. 3(b), the barrier 70 is shown in the compartment 32 positioned about the wide portion 41 and at an opposite side of the small container 50 as the spout 52. The barrier 70 operates as a spring force to exert a pressure against the small container 50 which forces the spout 52 of the small container 50 into the narrow portion 43 of the passageway 40. The barrier 70 can be placed into the compartment 32 before the small container 50 is placed in the compartment 32, as in FIG. 3(a). Or, the barrier 70 can be placed into the compartment 32 after the small container 50 is rotated and aligned with the narrow portion 43 of the passageway 40, as in FIG. 3(b). Once the spout 52 is in the narrow portion 43 of the passageway 40, the barrier 70 maintains the force on the small container 50 to prevent the spout 52 from entering the wide portion 41 of the passageway 40. When the small container 50 is rotated into the narrow portion 43 (FIG. 3(b)), the body portion 56 of the small container 50 is pushed by the barrier 70 toward the narrow portion 43 of the passageway 40. The spout 52 and passageway 40 can also be configured so that the small container 50 moves further into the barrier 70 when rotated so that the barrier 70 in return exerts a greater force on the small bottle 50 to better retain the small container 50 in position in the narrow portion 43 of the passageway 40.

Figure 6:
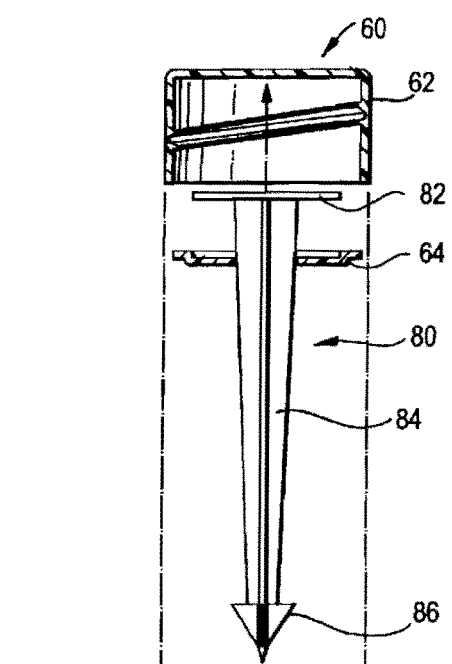
FIG. 6 is an exploded view of the small container and the release mechanism.
Figure 6:
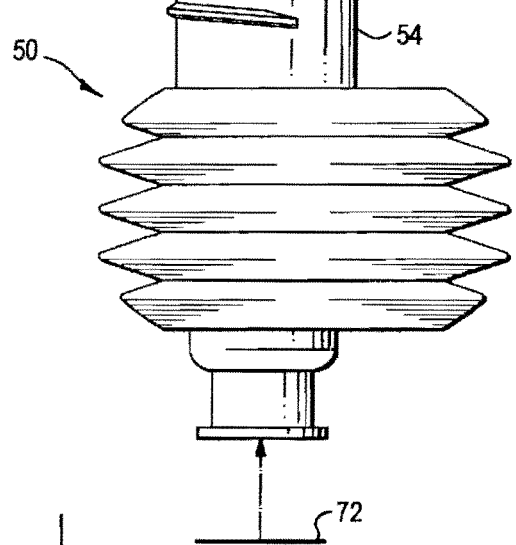

Turning to FIG. 6, the release mechanism 60 is shown. The release mechanism 60 includes a container cap 62, plunger 80 and retainer 64. The cap 62 is internally threaded to threadingly mate with the top end 54 of the small container 50. The cap 62 has side walls which form a center well. The plunger 80 is an elongated member having a head 82 at one end, prongs 86 at an opposite end and an intermediate portion 84 therebetween. The head 82 is a cylindrical section which is wider than the intermediate portion 84. The intermediate portion 84 and the prongs 86 have a cross- or plus-shaped cross-section. The intermediate portion 84 is wider at the top by the head 82 and tapered toward the bottom at the prongs 86. The prongs 86 form an arrow-like tip to the plunger 80 which can be relatively sharp.

Figure 7A:
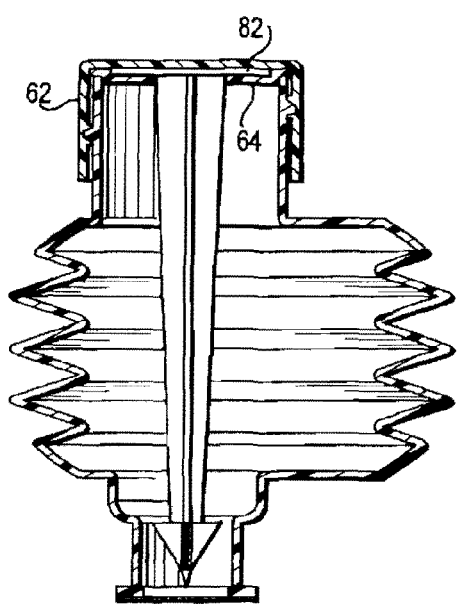
FIG. 7(a) is a sectional view taken along line W-W of FIG. 5 with the release mechanism engaged in the small container and in the ready position.

The retainer 64 is a cylindrical member with a center opening which receives the plunger 80. The center opening is smaller than the head 82 of the plunger, so that the head 82 cannot pass through the opening of the retainer 64. The retainer 64 is relatively flexible, but sufficiently rigid so that it can frictionally fit within the center well of the cap 62. The release mechanism 60 is assembled by placing the plunger 80 through the retainer 64 until the retainer 64 is against the head 82. The retainer 64 may have a central depressed portion which receives the head 82 of the plunger 80. As best shown in FIG. 7(a), the retainer 64 is then pressed into the well of the cap 62 until the retainer 64 and the head 82 are fully received in the well of the cap 62. The retainer 64 retains the head 82 in the cap 62 by virtue of the friction fit between the retainer 64 and the walls of the cap 62. In addition, the top leading edge of the walls of the head 82 press the retainer 64 against the inside top of the cap 62.

The operation of the system will now be described starting with FIG. 6, where the small container 50 is filled with a first liquid such as a concentrated cleaner with the bellows 59 in an expanded state. And, the large container 20 (FIG. 1) is filled with a second liquid such as a diluent. Sterile water is filtered at 0.2 microns into the main body reservoir 22 of the large container 20. The large container 20 is filled with the first substance through the opening 24 at the top of the large container 20. The large container 20 and the small container 50 are filled in two separate operations so that there is no accidental mixture of chemical agents. The contents of the containers 20, 50 thus remain separate until the mixing and dispensing apparatus 10 is ready for use by the user.

A concentrated chemical composition, such as a disinfectant, is filtered at 0.2 microns into the small container 50. The small container 50 has the foil 72 placed over the spout 52, so that the liquid remains within the small container 50 reservoir. In operation, the diluent and the chemical composition are assayed separately to ensure that proper formulations have been received. The composition and diluent are filtered with a 0.2 micron filter to remove particulates, and a particulate test is conducted. The composition and diluent are then measured to ensure that the proper dilution will result when they are eventually mixed together.

Turning to FIG. 7(a), the release mechanism 60 is then placed within the interior of the small container 50, with the plunger extending down through the intermediate portion 56. The release mechanism 60 is then engaged with the small container 50 by screwing the cap 62 onto the top end 54 of the small container 50. At that point, the top end 54 of the small container 50 is aligned with the spout 52 at the bottom end of the small container 50, so that the plunger 80 and prongs 86 are aligned with the spout 52 without touching the sides of the small container 50.

Once the small container 50 is filled and the release mechanism 60 is fixed to the small container 50, the small container 50 is placed inside the compartment 32 of the large container 20, as shown in FIG. 1. The spout 52 is aligned with the wide portion 41 of the passageway 40, FIG. 3(a), and the small container 50 is then rotated 180° so that the small container 50 is fixed within the narrow portion 42, FIG. 3(b). The barrier 70 maintains a pressure against the small container 50 so that the spout 52 does not come free of the narrow portion 42 of the passageway 40.

Figure 8:
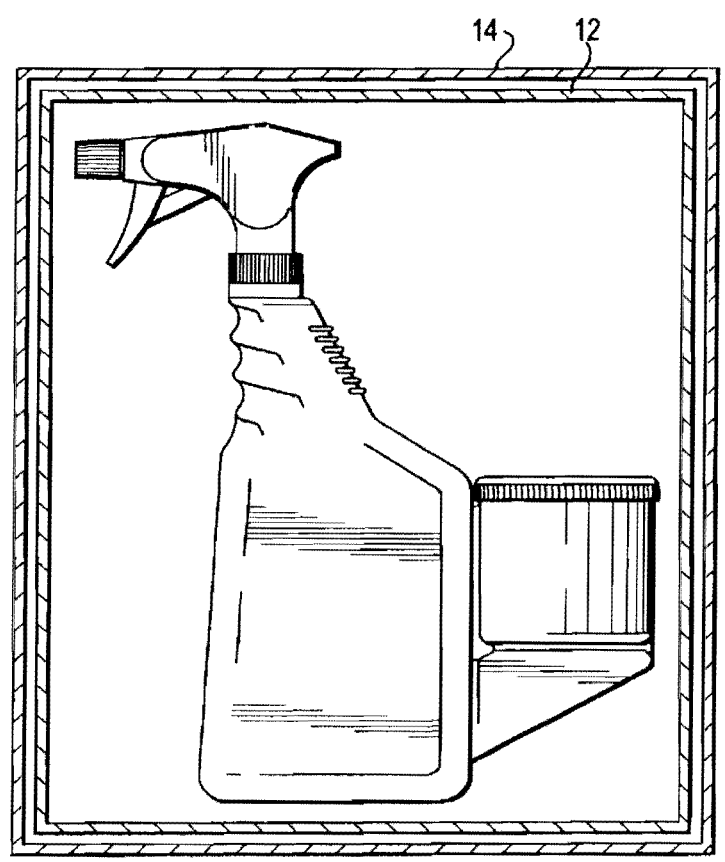
FIG. 8 is a side view of the apparatus contained within sealing layers.

Thus, as shown in FIG. 8, the apparatus 10 has the first liquid in the large container 20 and the second liquid in the small container 50, and with the small container 50 fixed to the large container 20. The apparatus 10 is not ready for use. Since the apparatus 10 will be used in a clean room, the apparatus 10 is irradiation sterilized. The apparatus 10 is placed in a first sealing layer 12 and hermetically sealed by heat to form a single layer sealed enclosure. The single layer sealed enclosure can then be inserted into a second sealing layer 14 and hermetically sealed by heat to form a second layer sealed enclosure. The first and second sealing layers 12, 14 are a polyethylene composition. Turning to FIG. 9, the double layer sealed enclosure can then be inserted into a carton 90 having a plastic liner 92. The plastic liner 92 is closed by tying or the like to form a third sealing layer. Finally, the carton is closed and prepared for shipping.

The carton 90 is then ready for irradiation, which is shown in FIG. 10. Gamma radiation is used since it has high penetration capability that enables relatively dense products or compositions to be processed easily. Sterilizing doses generally are in the 25-50 kGy (kilogray) range. To ensure proper dosage, the radiation is measured by dosimeters that measure the amount of irradiation impinging on the carton. The irradiation sterilizes the entire packaging, including the first, second and third sealing layers, the air contained within each layer, as well as the entire apparatus 10, the chemical composition in the small container and the diluent in the large container.

In this manner, when received at the operational site, the closed cartons may be opened and the liner 92 with the double-bagged chemical containers 10 contained therein may be removed on a loading dock prior to entry into a clean room area and the carton 90 discarded. The chemical containers 10 are maintained within the closed third sealing layer or liner 92 until removed and then brought to a clean room operating site. The liner is used in the preferred embodiment to prevent carton particles from contaminating the outermost sealing layer 14. Depending on the particular application, the carton liner 92 need not be used, e.g., when sterility of the exterior of the sealing layer 14 is of no concern.

Once transported into the clean room area or other operational site, the third sealing layer may be removed and the container 10 within the first and second sealing layer enclosures 12, 14 may be placed on a shelf for future use. When placing the sealed container enclosures on the shelves for use in clean rooms, generally sterilized gloves are used, however, these in themselves as well as the atmosphere of clean rooms have various particulates, such as microbes or bacteria, which dictate a relatively short shelf life for container 10 if only a single first layer 14 were formed around the container 10. However, with the first and second layers 12 and 14, the now somewhat less than sterilized second layer sealed container enclosure may be kept on the shelf for an indefinite period of time prior to use of the contents of the container 10.

Once the contents of the container 10 are to be used, the second sealing layer 14 may be stripped from the second layer sealed container enclosure leaving the first layer 12 surrounding and encasing the container 10 in a sterilized manner. Use then can be made of the contents of container 10 with the assurance that such has been maintained in a sterilized state.

Figure 7B:
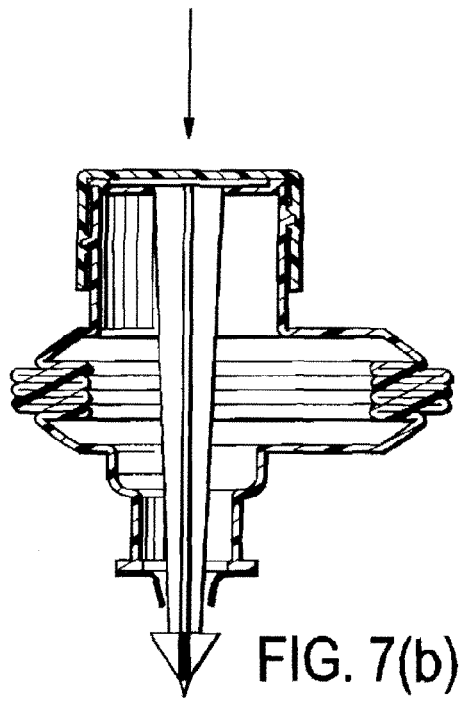
FIG. 7(b) is a sectional view taken along line W-W of FIG. 5 with the small container compressed and the release mechanism breaking the foil seal over the small container spout.

At this point, the user can use the contents of the containers 20, 50, which are sterile, as follows. The cap 36 of the compartment 32 is removed to grant access to the small container 50. Turning to FIG. 7(b), the user presses downward on the cap 62 of the small container 50 in the direction of the arrow shown. This compresses the bellows 59 and moves the top end 54 closer to the bottom spout 52. Eventually, the prongs 86 of the plunger 80 contact and pierce the foil seal 72 of the spout 52 to create an opening in the foil seal 72. The plunger 80 continues to push through the foil seal 72 and can continue to extend through the spout 52 to ensure that a large opening is made in the foil 72. Because the plunger 80 and prongs 86 have "+" shaped cross sections, there is plenty of space between the plunger and prong walls and the opening created in the foil 72 for liquid to pass out of the spout 52 past the plunger 80 and the prongs 86.

The user continues to push down on the top of the small container 50 until the bellows 59 are fully compressed, as shown in FIG. 7(b). The pushing (as well as gravity) forces the contents of the small container 50 out through the spout 52. It is not necessary to provide an air vent in the small container 50 since the fluid is emitted by the compression of the small container 50. Since the spout 52 is in direct flow communication with the neck 34 of the large container 20, the contents of the small container 50 are discharged directly into the contents of the large container 20. The contents of the small container 50 are discharged by the compression of the small container 50, even if diluent is present in the neck 34 and compartment 32. The user then replaces the cap 36 on the compartment 32 and if desired, can shake the entire apparatus 10 to further combine the contents of the two containers. The thus mixed contents can then be dispensed from the large container 20 through the dispensing mechanism 26 via the dip tube 28.

Chemical compositions can also be aseptically processed when being filled into the apparatus 10. The chemical composition can be filter sterilized, and the apparatus 10 sterilized by radiation. The composition can then be filled into the containers in a clean environment, and then placed in sterilized successive sealing layers that are hermetically sealed, and placed in a carton having a liner. All components in the aseptic filling operation are presterilized via gamma radiation and transferred to the clean (usually Class 100) aseptic filling environment, other than the composition, which is filter sterilized. In such area, all personnel are completely gowned in presterilized coveralls, hoods, boots, masks and goggles. The clean room is monitored for particulates and microbials. However, aseptic processing is generally more complicated and labor-intensive, and therefore is more appropriate for compositions that are not suitable for sterilization through irradiation, such as peracetic acid and hydrogen peroxide.

Thus, in both the terminal irradiation and the aseptic processing, the mixing occurs just prior to actual use, so that the mixture is fresh and effective. The mixture is made under sterile conditions inside the sterile container, so that the resulting mixture is sterile. In addition, the contents are measured when filled into the apparatus. Thus, the user does not have to make any measurement of the chemical composition or the diluent in the clean room, and can still be certain that the proper assay is achieved.

A foil 72 is utilized since it doesn't break or shatter, but instead pierces when contacted by the prongs 86. Thus, there are no loose pieces of the foil 72 or the prongs 86 which might otherwise enter into the liquid contents and contaminate the clean room. In addition, by using the dip tube 28 and the spray mechanism 26, no foreign particles are able to enter the clean room. In addition, a filter can be placed over the end of the dip tube 28 to further filter any particles that might be in the liquid. And, while the invention has been described for use with a spray bottle, other suitable containers can be utilized such as a gallon container having a filter over the spout for pouring.

Any suitable configuration of the apparatus 10 can be made, without departing from the spirit and scope of the invention. For instance, the small container need not be a separate container, but can be a compartment that is integral to the large container. However, the apparatus 10 is advantageous since it requires minimal manipulation by a user who is fully gowned in a clean room and wearing gloves. All the user needs to do is open the top of the compartment 32 and push down on the small container 50. The small container 50 and bellows 59 are sufficiently rigid to stand independently, and is protected by the compartment 32 during transport to prevent inadvertent or unintended collapse of the small container 50.

It is further noted that the mixing and dispensing apparatus 10 is easy to actuate by the gloved hand. The apparatus 10 substantially maintains the shape of a standard spray bottle. So, the user can easily grasp the top of the bottle and use the actuating spray handle without interference by the compartment 32 and the small container 50. In addition, the small container 50 and compartment 32 are cylindrical, but that other suitable shapes can be utilized. In addition, the large container 20, the plunger 80 and the small container 50 are each single unitary molded pieces made of plastic.

In accordance with the preferred embodiment, the apparatus 10 is about 13 inches tall from the bottom to the top of the dispensing mechanism 26. The main body portion is about 4.5 inches wide up to the junction 33 with the neck 34, and about 3 inches deep. The compartment is about 2.75 inches in diameter, and the small container 50 has a diameter of about 2.25 inches. The barrier 70 is 3 inches in length by about 1.75 inches tall.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A mixing and dispensing apparatus, comprising:
    a first container retaining a first substance;
    a second container retaining a second substance different than the first substance, the second container having a plunger and a spout, the plunger being configured to open the spout to release the second substance into the first container; and
    an angled neck extending between and in fluid communication with the first container and the second container, the spout of the second container in fluid communication with the angled neck.

2. A mixing and dispensing apparatus according to claim 1, wherein the second container is compressible.

3. A mixing and dispensing apparatus according to claim 1, wherein the angled neck extends from a longitudinal side of the first container.

4. A mixing and dispensing apparatus according to claim 1, wherein the angled neck is integrally formed with the first container.

5. A mixing and dispensing apparatus according to claim 1, wherein the first substance is sterile water and the second substance is a concentrated cleaner.

6. A mixing and dispensing apparatus according to claim 1, wherein the first container includes a dispensing mechanism, the dispensing mechanism includes a tube extending into the first container.

7. A mixing and dispensing apparatus according to claim 6, wherein the compartment of the first container is oriented substantially parallel to the tube in the first container.

8. A mixing and dispensing apparatus according to claim 1, wherein the second container is spaced from the main body of first container.

9. A mixing and dispensing apparatus according to claim 8, wherein a web extends between the first container and the main body of the first container.

10. The apparatus of claim 1, wherein said first container has a compartment and the second container is in the compartment of the first container.

11. The apparatus of claim 10, wherein the compartment has a passageway, and the spout extends through the passageway.

12. The mixing and dispensing apparatus of claim 1, wherein the first container has a main body portion retaining a first substance and a first opening and second opening, and wherein the spout of the second container is closed and in fluid communication with the angled neck through the second opening, such that the first substance or combined first substance and second substance can be dispensed through the first opening of the first container.

13. The mixing and dispensing apparatus of claim 12, wherein said first container has a compartment and the second container is in the compartment.

14. A mixing and dispensing apparatus, comprising:
a first container retaining a first substance;
a second container retaining a second substance different than the first substance, the second container having a plunger and an opening, the plunger being configured to release the second substance into the first container through the opening; and
a neck extending between and in fluid communication with the first container and the second container, the opening of the second container in fluid communication with the neck.

15. A method of mixing and dispensing a sterilized composition within a cleanroom, comprising the steps of:
providing an apparatus including:
a first container having a main body portion and a compartment,
a second container in the compartment of the first container and having a closed spout extending through a passageway in the compartment and in fluid communication with said main body portion of said first container,
an angled neck extending between and in fluid communication with the first and second containers, and
a plunger;
filling the main body portion of the first container with a first liquid;
filling the main body portion of the second container with a second liquid;
placing the plunger in the second container and aligning the plunger with the closed spout;
applying downward pressure to the plunger, such that the plunger opens the closed spout to release the second fluid into the main body portion of the first container, whereby the first and second fluids mix to form a sterilized composition.

16. The method of claim 15, wherein the first fluid is different than the second fluid.

17. The method of claim 15, wherein the first fluid is sterile water and the second fluid is a concentrated cleaner.

18. The method of claim 15, wherein the second container includes a compressible member upon which the downward pressure is applied.

19. The method of claim 15, further comprising the step of actuating a dispensing mechanism of the first container, such that the sterilized composition is expelled from the first container through the dispensing mechanism into the cleanroom.

20. The method of claim 19, wherein the dispensing mechanism is a spray head that has a trigger and an adjustable nozzle through which the sterilized composition is expelled.

21. The method of claim 20, wherein the apparatus further comprises a dip tube extending from the dispensing mechanism into the main body portion of the first container, such that the sterilized composition is drawn into the dip tube when the dispensing mechanism is actuated.

* * * * *